United States Patent
Smith et al.

(10) Patent No.: US 6,927,846 B2
(45) Date of Patent: Aug. 9, 2005

(54) REAL-TIME ON-LINE SENSING AND CONTROL OF EMULSIONS IN FORMATION FLUIDS

(75) Inventors: James Kevyn Smith, Houston, TX (US); Thomas H. Lopez, Houston, TX (US); C. Mitch Means, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 10/627,852

(22) Filed: Jul. 25, 2003

(65) Prior Publication Data

US 2005/0018176 A1 Jan. 27, 2005

(51) Int. Cl.⁷ .......................... G01N 21/41; G01N 21/55
(52) U.S. Cl. ........................................ 356/128; 356/445
(58) Field of Search .............................. 356/128, 136, 356/445; 95/23

(56) References Cited

U.S. PATENT DOCUMENTS

| | | | |
|---|---|---|---|
| 4,419,265 A * | 12/1983 | Diery et al. ................. | 516/158 |
| 4,737,265 A | 4/1988 | Merchant, Jr. et al. ..... | 208/188 |
| 5,026,139 A * | 6/1991 | Klainer et al. .............. | 356/128 |
| 5,643,460 A | 7/1997 | Marble et al. .............. | 210/705 |
| 5,712,703 A | 1/1998 | Ando et al. .................. | 356/319 |
| 5,712,934 A | 1/1998 | Johnson ........................ | 385/12 |
| 5,831,743 A | 11/1998 | Ramos et al. ................ | 356/445 |
| 5,841,666 A | 11/1998 | Perdue et al. ........... | 364/551.01 |
| 5,919,707 A * | 7/1999 | Banks et al. ................. | 356/320 |
| 5,921,912 A | 7/1999 | Hart et al. .................... | 516/176 |
| 6,176,323 B1 * | 1/2001 | Weirich et al. ............... | 175/40 |
| 6,467,340 B1 * | 10/2002 | Gallagher et al. ........ | 73/152.18 |
| 2003/0051602 A1 * | 3/2003 | Means ........................... | 95/23 |
| 2003/0071988 A1 | 4/2003 | Smith et al. ................. | 356/128 |
| 2004/0098202 A1 * | 5/2004 | McNeil et al. ................ | 702/12 |

FOREIGN PATENT DOCUMENTS

| | | | | |
|---|---|---|---|---|
| EP | 0262670 A1 | | 4/1988 | |
| GB | 2 199 404 A | * | 7/1988 | .......... G01N/21/43 |
| JP | 57142546 | | 9/1982 | |
| JP | 03-186734 A | * | 8/1991 | .......... G01N/21/43 |
| JP | 07109955 | | 4/1995 | |

* cited by examiner

Primary Examiner—Gregory J. Toatley, Jr.
Assistant Examiner—Kara Geisel
(74) Attorney, Agent, or Firm—Madan, Mossman & Sriram, P.C.

(57) ABSTRACT

Real time determination of the presence of emulsion in a formation fluid is accomplished using an optical probe, preferably an attenuated total reflectance probe. The determination can then be used to appropriately increase, decrease or leave unchanged the use of demulsification additives or other means to control emulsion formation. The method is particularly useful for free water knock-out separations, where a plurality of probes can be used to distinguish the location and/or volume of emulsion, or "rag", layer and thereby to facilitate decantation of relatively pure oil and water fractions. It can also be effectively used in pipelines, and can optionally determine the degree of emulsification and trends toward emulsification or demulsification.

12 Claims, 1 Drawing Sheet

REAL-TIME ON-LINE SENSING AND CONTROL OF EMULSIONS IN FORMATION FLUIDS

BACKGROUND OF THE INVENTION

1. Field of the Invention

This invention relates to a method for use in oilfield and pipeline operations to monitor and control emulsion formation in formation fluids. This invention particularly relates to a method for monitoring and controlling emulsions originating from formation fluids located downhole or contained in pipelines, free water knock-outs and other separation equipment.

2. Background of the Art

Fluids that are typically first recovered from a wellbore in oilfield recovery operations generally consist primarily of crude oil and water. Such fluids are referred to herein as "formation fluids". These fluids may also contain a number of additional components, such as water insoluble materials in the form of colloidal suspensions, but these are generally very minor components. Thus, one of the first steps in recovery of the oil fraction, which is often a primary goal of such recovery operations, is to separate the oil from the water. This step substantially reduces the volume of material that must undergo further processing and also simplifies further processing of the oil.

Fortunately, water and oil are not miscible and tend to separate into two distinct phases. In order to capitalize on this natural tendency, those skilled in the art of oil recovery operations employ vessels wherein the formation fluid can stand for a period of time. These vessels are designated as "free water knock-outs". The separation results in a distinct water layer at the lowest vessel level; a distinct oil layer at the uppermost vessel level; and an interface between the two which constitutes an emulsion, i.e., a dispersion of oil and water droplets, often with one component predominating as a continuous phase, and the other phase predominating as a discontinuous phase. This emulsion layer is often alternatively referred to as the "rag layer". The separated oil and water can be easily removed from the free water knock-out, but it is desirable to ensure that the emulsion layer remain in the free water knock-out where it cannot contaminate either of the recovered oil or water products.

Furthermore, considering the scale of oil recovery operations, it is not surprising that the rag layer is often substantial and, therefore, contains a considerable amount of economically valuable recovered oil product. Thus, it is desirable to quantitatively reduce this layer as much as possible in order to optimize oil recovery. Such reduction effort can include addition of demulsification additives such as alkyl phenol resins, e.g., oxy-alkyl phenol resins. Since a certain amount of emulsification results from the increased shear of higher pump rates, it is also possible to reduce emulsification by reducing pump rate.

Previously, significant demulsification has often been difficult. This is, in part, simply because inflow and outflow from the free water knock-out are typically maintained continuously. During the process the oil is recovered from an upper oil outflow pipeline and the water is recovered from a lower water outflow pipeline. Such outflow piping, designed for simple decantation, obviously does not distinguish between the three layers. The result is that some of the emulsion layer can easily creep in with the oil-only layer and/or with the water-only layer during the separation process.

In view of difficulties in obtaining relatively pure decantation products, it would be desirable in the art to find a way to easily detect and identify emulsion in a formation fluid, whether such emulsion is present as a discrete emulsion, or "rag", layer in a free water knock-out or at another point in the transport of a formation fluid. The ability to identify emulsion could then be used to enable control of the emulsion, including reduction of contamination of decantation products and/or effective demulsification.

SUMMARY OF THE INVENTION

The present invention provides in general a method to detect emulsion and/or to quantify or qualify its presence to enable effective separation, with or without prior demulsification, and removal of the oil and water as distinct phases. It is a method for real time determination of emulsion in a formation fluid comprising first positioning an optical probe, having a probe surface which can measure changes in total internal light reflectance, such that the probe surface is in contact with a formation fluid, wherein the probe and its surface are composed of material which can withstand an extended period in contact with the formation fluid. The total internal light reflectance at the probe surface is measured, and that measurement can be interpreted to determine in real time whether an emulsion is present and/or the degree of emulsification at such surface.

In another embodiment, the present invention is a method for controlling emulsion formation in a formation fluid comprising placing an optical probe, having a probe surface which can measure changes in total internal light reflectance thereat, in contact with a formation fluid; measuring the changes in total internal light reflectance at the probe surface; determining in real time the emulsion presence in the formation fluid as a function of the changes in total internal light reflectance at the probe surface; comparing such determination to a predetermined maximum acceptable emulsion presence; and effecting a change in the rate of addition, if any, to the formation fluid of an additive effective to reduce the emulsion presence. In this embodiment, too, the probe is composed of a material which can withstand an extended period of contact with the environment to which it is exposed. The rate of addition, if any, to the formation fluid of a demulsification additive can thereby be appropriately increased when the emulsion presence is greater than the predetermined maximum acceptable emulsion presence, or decreased or maintained when no emulsion is detected or when the emulsion presence is less than the predetermined maximum acceptable emulsion presence.

In still another embodiment the invention is a system for controlling emulsion formation in a formation fluid, comprising a fluid flow path for flowing formation fluid recovered from a subsurface formation; an optical probe, having a probe surface that can measure changes in light reflectance at the probe surface, in contact with the formation fluid; a processor associated with the optical probe enabling collection of data therefrom, such data corresponding to the presence of emulsion or degree of emulsification in the formation fluid; and a controller associated with the processor enabling translation of data therefrom to initiate action to modify the presence of emulsion or degree of emulsification. Preferably the optical probe, including its surface, is composed of material which can withstand an extended period of contact with the environment to which it is exposed.

The invention is particularly useful because it enables determination of both the existence and the location of the emulsion relative to other phases in the formation fluid and can also be used to detect the degree of emulsification and trends toward emulsification or demulsification. Determining these characteristics enables more effective demulsification, if desired, and ultimately leads to cleaner separations of the oil and water phases of the formation fluid.

BRIEF DESCRIPTION OF THE DRAWING

For a detailed understanding and better appreciation of the present invention, reference should be made to the following detailed description of the invention and the preferred embodiments, taken in conjunction with the accompanying drawing.

DETAILED DESCRIPTION OF THE EMBODIMENTS

Figure 1:
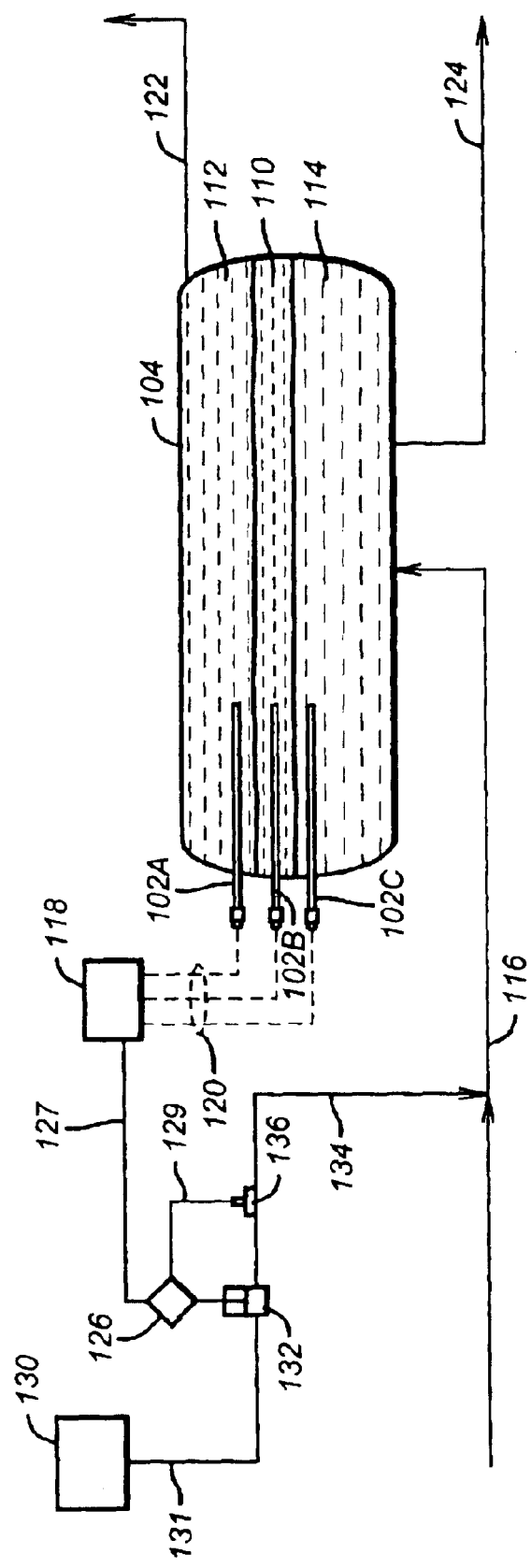
FIG. 1 is a schematic illustration of a wellsite system for monitoring the quantity and location of emulsion present in a free water knock-out vessel according to one embodiment of the present invention.

In general, in the practice of the present invention an optical probe, having a probe surface that can measure changes in total internal light reflectance at the probe surface, is placed in contact with a formation fluid that has been produced from an oil well. The refractive index of a material is defined as the ratio of the speed of light in a vacuum to the speed of light in the given material. The present invention utilizes changes in the refractive index in the sample medium, defined here as the emulsion, to elicit changes in the intensity of the total internal reflection signal. If the formation fluid in contact with the probe is crude oil, or if it is brine, the total internal reflected light intensity contained within the probe will not be affected, and thus no change in signal will be recorded. If, however, the formation fluid in contact with the probe is an emulsion, the total internal reflected light intensity contained within the probe will be attenuated, and thus a change in the signal will be recorded. In general the presence of emulsion results in a total internal reflectance measurement that is significantly lower, at a variety of wavelengths, than that of either oil or brine alone.

The method of the present invention finds particular use in systems where successive measurements are made by one probe, or where two or more probes are employed. In these systems such real time indications of the presence of emulsion can be monitored for change. Any change indicates an increase or decrease in the amount of total emulsion and/or degree of emulsification (that is, the relative proportions of the oil and water phases present in the emulsion), depending upon how the probes are set up. Such increase or decrease could be ascribed to changes in the quality of the formation fluid as it is extracted from the formation, or to other factors such as pump rate. However, regardless of its cause, changes in measurements generated by the probe enable the skilled practitioner to interpret therefrom whether remediation of any type is needed.

Such remediation could include initiation or increase of a demulsification treatment. Treatment options can include, for example, injection of a demulsification additive into the transport line, or reduction of pump rate. Decrease of emulsion at a given probe site or as indicated by different readings at different sites along the formation fluid's flow path might indicate that demulsification treatment can be reduced or stopped. If there is no change in the emulsion level, the level of treatment, if any, could simply be maintained.

The skilled practitioner will know that some variations in emulsion quantity or quality may be unavoidable. In such cases it is possible that variation can be tolerated, within certain prescribed limits. Such limits would be predetermined based upon a variety of factors including foreknowledge of the particular formation being tapped, economics of demulsification treatments, effectiveness of a given free water knock-out system, and the like. The skilled practitioner can thus easily determine a maximum acceptable emulsion presence for any given system and employ that determination in practicing the method.

In the practice of the present invention an optical probe is used to measure the total internal light reflectance at the probe surface. Probes useful in the invention include any having a probe surface capable of obtaining this measurement. In a preferred embodiment, an attenuated total reflectance ("ATR") probe is selected.

Where an optical probe of any type is selected, the probe includes a photometer, which is the instrument that generates the incident light and receives the transmitted light, thereby measuring the difference between the two. In the case of an ATR probe, the photometer measures the attenuated total reflectance, which is defined as the ratio of the intensity of the light which is reflected within the probe in the absence of an emulsion to the intensity of the light in the presence of an emulsion. In the absence of an emulsion, light is reflected at the crystal sample interface back into the crystal medium. In this instance, light intensity is 100%. In the presence of an emulsion, a certain proportion of light intensity is attenuated, thus resulting in an overall loss in light intensity returned to the detector. In this instance, light intensity is 100%-x, where x depends upon the concentration of the emulsion at the crystal interface, refractive index of the emulsion, or both. Photometers useful with the present invention include single wavelength photometers, spectrophotometers, UV-VIS-NIR spectrophotometers, and the like. Any of these photometers can be included as part of the ATR probe, resulting in a device capable of identifying an emulsion and distinguishing the emulsion from other liquid phases with which it may be in contact.

In employing an ATR probe it is preferred that the light being directed through the probe's crystal surface has a wavelength from about 400 nm, more preferably about 500, and most preferably about 640 nm, to about 1500 nm, more preferably about 900, still more preferably about 700, and most preferably about 680 nm. These wavelength ranges generally include both the visible and infrared spectral regions. These preferences have been confirmed experimentally and illustrate the fact that the attenuated total reflectance of most emulsions of this type (oil/water) can be conveniently and efficaciously measured using a light wavelength of about 660 nm.

The probe surface is preferably a crystal, although in some embodiments another type of sensor can be used. Where a crystal is selected, it is most often synthetic sapphire. Other materials are also suitable, including, for example, other natural or synthetic carborundums, provided that their crystal matrices are sufficiently homogeneous to minimize or eliminate the occurrence of events which may reduce the accuracy of the reflectance measurement. It is important that the probe surface, and in many cases any other portion of the probe body in contact with the formation fluid, be composed of material that can withstand the conditions of the environment, including temperature and pressure, to which such will be exposed.

The geometry of the probe crystal is also significant in ensuring the desired sensitivity to changes in reflectance. For purposes of the present invention, a trapezoidal, rather than dome-shaped, crystal is desirable to maximize the clarity of the signal received. If the crystal is trapezoidal, i.e., a quadrilateral having only two sides parallel, the surfaces exposed to the formation fluid are its top and angled sides. This shape tends to minimize the small but measurable amount of light-scattering that occurs at curved surfaces, which tends to "blur" the measuring signal. The base of the trapezoidal or other crystal is attached to the probe body.

Other factors affecting the accuracy of the probe's measurement include, in particular, its light source bandwidth. Narrower bandwiths tend to increase accuracy.

Overall, the clarity and precision of the required signal will ultimately determine the suitability of a given material or design. For many purposes, especially in free water knock-outs, particular accuracy of measurement is significantly less important than simple detection of any change in light reflectance. This gross reporting of such change may adequately serve the needs of the skilled practitioner.

In the practice of the present invention the light emitted by the photometer (incident light) passes through the probe's crystal and, at its surface, contacts the surface of the formation fluid being monitored. Light transmitted back to the photometer (transmitted light) is then quantified in terms of its intensity. This quantification is referred to herein as spectral data. It is particularly convenient to locate both light source and photometer at a single site and, most conveniently, in a single unit. The activites of generating a given intensity of light, transmitting it through the probe's crystal, and measuring its after-transmission intensity together constitute what is hereinafter referred to as "detection". The total detection path length may vary, depending on the desired physical locations of each and any limitations imposed by the wavelength of the light being employed.

An ATR probe is preferred for the practice of the present invention because it is readily available, reasonably economical in many embodiments, and permits both laboratory measurements and real-time direct measurements of reflectances. Because crude oil may range from dark-colored and relatively opaque to very light-colored and translucent or even transparent, depending upon the particular oilfield being tapped, it is often preferred to carry out laboratory measurements using samples prior to performing such real time measurements. Such laboratory measurements can then be taken into account to ensure that the spectral data is meaningfully interpreted. It is also desirable to take into account the effect on reflectance of other formation fluid components. These commonly include salts, asphaltenes, waxes, rheology control additives, and the like. While it is theoretically possible that fluorescence or phosphorescence exhibited by the formation fluid could affect the accuracy of the measurement, such is not significant in most instances.

The actual measurement of the spectral data received from the probe can be expressed in a variety of ways. For example, it can be expressed as a single point at a selected wavelength; as points at a plurality of wavelengths within the range disclosed herein; as an infinite number of points representing an entire spectrum between two wavelengths; or as some combination thereof. Where high accuracy in determination of degree of emulsification is desired, it is preferred that the spectral data be expressed as an infinite number of points representing an entire spectrum between two wavelengths.

The present invention is therefore highly adaptable. Through its use it is possible to determine not only the presence of an emulsion and to quantify that emulsion, but also to qualify that emulsion, which herein means to determine the degree of emulsification. A small degree of emulsification would refer to one in which one phase significantly predominates, while a high degree of emulsification refers to one in which neither phase significantly predominates. Spectral data can be used distinguish between these degrees as desired.

Following detection, the spectral data is preferably transmitted to an appropriate interpretation means. Such interpretation means can include, for example, any means capable of translating the electrical, electronic, electromagnetic, fiber optic, or other type of signal from the probe to a measurement. This interpretation means can be, for example, a microprocessor or a computer, and for convenience is hereinafter referred to as a processor.

The processor may interpet the data on various bases. For example, such interpretation may include comparison with or reference to calculated or modeled measurements. Where a calculated figure is used, such may be theoretical or based upon extrapolation or interpolation of a calibration curve. Also useful is reference to laboratory analytical data of the actual fluid being monitored. Particularly where emulsion control is critical, such laboratory data may be produced via intermittent sampling of the formation fluid. Such sampling may be inconvenient, however, in the typically closed system employed in the oil patch. Other embodiments of the present invention may employ one or more previous analyses from the same or a similar system as a reference.

In preferred embodiments of the present invention the processor is connected with a control means, hereinafter referred to as a controller. The controller has the capability of translating the data received from the processor into appropriate commands that actuate changes in, or maintenance of, one or more system variables. Such variables can include demulsifier level, pump rate, temperature, pressure, and the like. Typically such controller is electrical or electronic in nature and may be responsive to the processor by wireless or hardwired means. As in the processor that is part of the detection activities of the present invention, the controller's translation capability is typically enabled by a microprocessor or computer. In preferred embodiments, the processor and controller are incorporated into a single unit, which may be remote from the probe location. In such embodiments the combination instrumentation can be referred to as a "processor/controller".

As already noted hereinabove, emulsion formation or maintenance may be tolerated within a specified range. Factors affecting emulsion measurements include the identification and fluctuation in composition of the formation fluid; the equipment; pump rate; well history; accuracy of the ATR device; operating experience of a particular well, pipeline or storage facility; effectiveness of a particular treatment; combinations thereof; and the like. Of particular significance in the practice of the present invention is the fact that operator intervention is generally not needed to carry out its activities resulting in both measurement and control. Thus, operator involvement can desirably be limited substantially to verifying the accuracy of the probe output to the processor.

An important embodiment of the present invention is a system for controlling emulsion in formation fluids. Such system includes a detection means (in preferred embodiments, an optical probe); a processor to interpret the detection data; a controller to translate the processor's data into action to modify the emulsion presence as desired; and, optionally, a means to ensure that the probe surface is not occluded, i.e., a means to clean the probe. These basic elements can involve, incorporate or employ a wide variety of computers, signal transmitters and receivers, computational programs and software. Other devices capable of sending and/or receiving electromagnetic, electrical, electronic, fiber optic or mechanical commands, instructions or signals, and which can be controlled either manually, non-manually, or both, can also be incorporated into a complete system for controlling the presence and/or amount of emulsion in the formation fluid at any or many locations and at any or many points in time.

In the present invention the location of the probe or probes being used for detection purposes is important in determining the accuracy and applicability of the spectral data received therefrom. When the present invention is employed in connection with a free water knock-out, it is preferred that three ATR probes are used at three distinct locations in real time for comparison. For example, one probe can preferably be located where the crude oil layer would be anticipated, one where the emulsion ("rag") layer would be anticipated, and one where the water layer would be anticipated. In this case, the probes serve to warn of any phase change occurring at any of the given locations. Such a phase change can therefore indicate either movement of the emulsion layer or a general increase, or decrease, in its volume. Appropriate steps can then be taken to prevent the potential contamination of the desired separated oil and water phases upon decantation from the free water knock-out.

Alternatively, again in the case of a free water knock-out, a probe can be physically moved across a given field within the vessel. This movement is preferably at a predetermined rate of speed to enable determination of not only the presence of an emulsion layer, but also of the thickness thereof. This data can then be employed to ensure that the oil and water layers remain in their desired discrete locations within the free water knock-out. Additionally or alternatively, the data can be used to determine the type and amount of demulsification treatment needed, if any.

In another embodiment, where it is desired to monitor a pipeline transporting a formation fluid, it is again preferred that at least two, and possibly more, probes be employed. In this case the probes serve to indicate the presence of an emulsion and to provide an upstream warning of imminent change in the degree of emulsification. Such upstream warning can be used to actuate appropriate remediation. For example, in a system where the upstream spectral data indicates the degree of emulsification is increasing, demulsifier can be injected or increased, and its effectiveness measured via the downstream probe's data. In contrast, where the upstream spectral data indicates the degree of emulsification is decreasing, demulsifier level can be reduced or discontinued. Similarly, other remedial actions can be taken, discontinued, increased or decreased as appropriate.

In view of the adaptability of the present invention, it is therefore within its scope to use one or more probes to monitor a formation fluid, prior to or after treatment to separate the oil and water phases. The result of such monitoring determines (a) if emulsion is present; (b) whether such emulsion is increasing or decreasing, in quantity and/or degree; (c) whether a treatment is needed or needs to be changed, and/or whether other conditions to which the fluid flow is exposed need to be changed; and (d) the appropriate level of such treatment. Such monitoring can effectively occur in a pipeline and/or in its associated equipment such as in a free water knock-out.

While the present invention is used to provide direct real-time determinations of the presence, degree, or even rate of emulsion formation, these determinations may not need to be made on a continuous basis. Other modes of operation can be employed. These include, for example, semi-continuous, intermittent, or as-needed determinations. It is also possible to tailor the determinations to combinations of these operational modes. Formation fluid composition and changes in the composition, operating experience, and maintenance requirements are just some of the factors that can influence the frequency of the determinations.

It is important to note that, to maximize accuracy of the probe output, it is necessary to ensure that scaling or other occluding deposition has not occurred on the surface of the probe's crystal prior to obtaining the signal therefrom. Scaling can occur when minerals present in the formation fluid precipitate on the crystal. While such cleaning can be done manually, such may be inconvenient, particularly if the formation fluid flow path is closed. Thus, it is often preferred that such cleaning be effected automatically. Automated systems, such as the Welker® AID-1 system, that automatically extracts the probe, cleans its surface using both chemical and mechanical means, and reinserts it thereafter, are recommended and can be triggered by a controller that monitors the surface of the probe based on artifacts in the readout from the processor that are characteristic of the presence of occlusions. Alternatively, the cleaning can also be done on a simple time schedule.

Whether the probes are cleaned manually or automatically, the removal of the scale or other occlusion can be done using appropriate reagents and solvents. For example, if a calcium carbonate scale has formed, it can be removed using a dilute acid such as hydrochloric. Any method known to those skilled in the art of cleaning scale from surfaces can be used with the methods of the present invention. Scale control additives can, and typically are, added to the formation fluids, and the presence of these also serves to reduce or eliminate the occurrence of occlusions. These additives can include, for example, phosphate esters, phosphonates, poly maleic acid, poly acrylic acid, or other homo-, co- and ter-polymers, in various proportion.

FIG. 1 shows a preferred embodiment of the present invention. It is a schematic diagram of a system wherein the presence of, and quantification of, an emulsion is monitored with three ATR probes (102A, B and C). The ATR probes (102A, B and C) are located in a free water knock-out (104), with the first ATR probe (102A) located uppermost; the second ATR probe (102B) located below the first probe (102A); and the third probe (102C) located below the second probe (102B). Thus, in this application an emulsion layer (110) is anticipated to form, and desirably be discretely maintained, in the area of the second ATR probe (102B), while the first ATR probe (102A) monitors the oil layer (112) and the third ATR probe (102C) monitors the water layer (114).

Operation of the illustrated system includes introduction of a production fluid (generally a combination of oil and water) from a well header (not shown) via a production fluid inlet (116) that transports the production fluid to the free water knock-out (104). Upon standing in the free water knock-out (104) the production fluid separates into three distinct layers, including the oil layer (112), the emulsion layer (110), and the water layer (114). The three ATR probes (102A, B and C) are each in contact with one of these layers and transmit the data showing the internal light reflectance that confirms or disaffirms the identity of its respective anticipated layer to a processor (118) via appropriate transmission connections (120). If separation of the layers is satisfactorily achieved and maintained with the emulsion layer (110) between the oil layer (112) and the water layer (114), the oil layer (112) can be continually decanted via an oil outlet pipeline (122). Similarly, the water layer (114) can be continually decanted via a water outlet pipeline (124). The emulsion layer (110) desirably remains inside the free water knock-out (104).

If, however, the ATR probes (102A, B and C) show that the emulsion layer (110) has moved significantly higher or lower, or increased in volume such that it is now detected by two or all of the probes rather than just the one designated for that layer (which is 102B), the system can remedy the problem because a controller (126) is positioned to receive the interpreted detection signal, via a controller input connection (127), from the processor (118). Such signal is translated by the controller (126) and sent, via a demulsification input connection (128), to initiate, increase, decrease, or cease flow of a demulsification additive by a demulsification tank (130), via its tank outlet (131) through an injection pump (132) and into the production fluid inlet (116). Flow of the demulsification additive can be measured in the demulsification additive inlet (134) via a flowmeter (136), which communicates the flowrate back to the controller (126), via flowrate connection (129), where it can be compared to the desired flowrate as interpreted by the controller (126) based on the translated signal from the processor (118). Thus, precise control of the relative thickness of the emulsion layer (110) can be achieved to ensure that the decantation of the oil layer (112) and the water layer (114) from the free water knock-out (104) results in relatively pure products.

All of the signals and/or instructions from the controller can be communicated via methods known to those skilled in the art, and can include appropriate cables, optical fibers, and other electrical, electronic, mechanical or electromagnetic communications apparatuses. Alternatively, wireless communications are also comprehended as within the scope of the present invention, and may be particularly desirable to avoid equipment damage resulting from turbulence and other flow-induced mechanical forces. Furthermore, the detection, comparison and other operations to be applied to the data obtained by means of the sensor or probe can be automated with the assistance of appropriate devices such that, in one preferred embodiment, the entire system is automated. Even in the case of an automated system, however, it is both desirable and within the understanding of those skilled in the art to ensure the capability of manual intervention by an operator, either at the wellsite and/or at a remote location, to optimize performance or safety thereof. In other embodiments, additional backup can be provided by use of more than one detection and/or control means, which can include programming incorporated therein, to receive the detection output from the sensor and to interpret and translate that output to initiate appropriate action. Such backup units or programming can be onsite or at locations remote from the primary units. Communication with a second controller or processor can be accomplished using, for example, a remote data communications line.

In the embodiments of the present invention a plurality of demulsification additive sources and the respective pumps and metering devices to administer such can optionally be employed. These can be controlled individually or in concert with one another by one or more processor/controllers and/or separate controllers. Significantly, a single processor/controller or a single controller associated with two or more separate processors can be used to manage the emulsion presence at two or more wells at the same time.

It is further noted that while a part of the foregoing disclosure is directed to some preferred embodiments of the invention or embodiments depicted in the accompanying drawings, various modifications will be apparent to and appreciated by those skilled in the art. It is intended that all such variations within the scope and spirit of the claims be embraced by the foregoing disclosure.

What is claimed is:

1. A method for real time determination of emulsion in a formation fluid comprising: (a) positioning two or more optical probes, each probe having a probe surface that can measure changes in total internal light reflectance, such that the probe surfaces are in contact with a formation fluid, wherein each probe and its surface are composed of material that can withstand an extended period in contact with the formation fluid; (b) measuring the total internal light reflectance at each probe surface; and (c) determining in real time therefrom whether an emulsion is present or the degree of emulsification at such surface, wherein the optical probes are attenuated total reflectance probes located in a free water knock-out.

2. The method of claim 1, wherein the attenuated total reflectance probes include a photometer that measures light in a wavelength range of from about 400 to about 1500 nm.

3. The method of claim 2 wherein the photometer measures light in a wavelength range of from about 640 to about 680 nm.

4. A method for controlling emulsion formation in a formation fluid comprising: (1) placing two or more optical probes, each probe having a probe surface that can measure changes in total internal light reflectance thereat, in contact with a formation fluid; (2) measuring the changes in total internal light reflectance at the probe surfaces; (3) determining in real time the presence of emulsion in the formation fluid as a function of the changes in total internal light reflectance; (4) comparing the determination of (3) to a predetermined maximum acceptable emulsion presence; and (5) effecting a change in the rate of addition, if any, to the formation fluid of an additive effective to reduce the emulsion presence; wherein: (a) each optical probe is composed of a material that can withstand an extended period of contact with the environment to which it is exposed; and (b) the rate of addition, if any, to the formation fluid of a demulsification additive is: (i) increased when the emulsion presence is greater than the predetermined maximum acceptable emulsion presence; (ii) decreased or maintained when no emulsion is detected or when the emulsion presence is less than the predetermined maximum acceptable emulsion presence; wherein the optical probes are attenuated total reflectance probes located in a free water knock-out.

5. The method of claim 4 wherein the attenuated total reflectance probes include a photometer capable of measuring light in a wavelength range of from about 400 to about 1500 nm.

6. The method of claim 5 wherein the photometer is capable of measuring light in a wavelength range of from about 640 to about 680 nm.

7. The method of claim 4 wherein the demulsification additive is an alkyl phenol resin.

8. A system for controlling emulsion formation in a formation fluid comprising a fluid flow path for flowing formation fluid recovered from a subsurface formation; an optical probe, having a probe surface that can measure changes in light reflectance at the probe surface, in contact with the formation fluid; a processor associated with the optical probe enabling collection of data therefrom, such data corresponding to the presence of emulsion or degree of emulsification in the formation fluid; and a controller associated with the processor enabling translation of data therefrom to initiate action to modify the presence of emulsion or degree of emulsification wherein the fluid flow path comprises a free water knock-out and at least three optical probes are located inside the free water knock-out having an oil outflow pipeline and a water outflow pipeline, at positions such that a first probe is at or adjacent to the level of the oil outflow pipeline, a second probe is at or adjacent to the level of the water outflow pipeline, and a third probe is between the oil outflow pipeline and the water outflow pipeline.

9. The system of claim 8 further comprising an automated probe surface cleaning device capable of extracting, cleaning, calibrating and inserting or reinserting the probe surface.

10. The system of claim 9 wherein the optical probes are attenuated total reflectance probes.

11. The system of claim 8 wherein the optical probes are attenuated total reflectance probes.

12. The system of claim 8 wherein the processor and controller incorporated into a single unit.

* * * * *